(12) United States Patent
Turner

(10) Patent No.: US 9,332,997 B2
(45) Date of Patent: May 10, 2016

(54) MEDICAL DEVICE

(75) Inventor: Nicholas Turner, Devizes (GB)

(73) Assignee: Smith & Nephew plc, London (GB)

(*) Notice: Subject to any disclaimer, the term of this patent is extended or adjusted under 35 U.S.C. 154(b) by 821 days.

(21) Appl. No.: 12/374,381

(22) PCT Filed: Jul. 19, 2007

(86) PCT No.: PCT/GB2007/002763
§ 371 (c)(1),
(2), (4) Date: May 12, 2009

(87) PCT Pub. No.: WO2008/009959
PCT Pub. Date: Jan. 24, 2008

(65) Prior Publication Data
US 2009/0312780 A1      Dec. 17, 2009

(30) Foreign Application Priority Data

Jul. 20, 2006   (GB) .................................. 0614428.1

(51) Int. Cl.
| | |
|---|---|
| *A61B 17/32* | (2006.01) |
| *A61B 17/15* | (2006.01) |
| *A61B 17/56* | (2006.01) |
| *A61B 17/16* | (2006.01) |
| *A61B 17/17* | (2006.01) |
| *A61B 19/00* | (2006.01) |

(52) U.S. Cl.
CPC ........... *A61B 17/1668* (2013.01); *A61B 17/175* (2013.01); *A61B 2019/462* (2013.01); *A61B 2019/5416* (2013.01)

(58) Field of Classification Search
CPC ............. A61B 17/1668; A61B 17/175; A61B 2019/461; A61B 2019/462
USPC ............................................... 606/79, 89, 172
See application file for complete search history.

(56) References Cited

U.S. PATENT DOCUMENTS

| | | | | |
|---|---|---|---|---|
| 4,952,213 A | * | 8/1990 | Bowman | A61B 17/157 606/62 |
| 5,122,145 A | * | 6/1992 | Fishbane | A61B 17/6425 606/102 |
| 5,681,333 A | | 10/1997 | Burkhart et al. | |
| 5,683,397 A | * | 11/1997 | Vendrely | A61B 17/155 606/88 |
| 5,700,268 A | * | 12/1997 | Bertin | A61B 19/46 606/102 |
| 6,096,082 A | * | 8/2000 | Stegmuller | A61B 17/155 606/102 |
| 6,193,724 B1 | * | 2/2001 | Chan | A61B 17/175 606/102 |
| 6,632,226 B2 | * | 10/2003 | Chan | A61B 17/175 606/102 |

(Continued)

FOREIGN PATENT DOCUMENTS

| | | | | |
|---|---|---|---|---|
| JP | 2002102236 | 4/2002 | | |
| WO | WO 2004107993 A1 | * | 12/2004 | ........... A61B 17/175 |
| WO | WO2005089660 | 9/2005 | | |

*Primary Examiner* — Zade Coley
(74) *Attorney, Agent, or Firm* — Taft Stettinius & Hollister LLP

(57) ABSTRACT

A device (1) for indicating on an object to be cut the cutting depth of a cutting tool, the device comprising: a first arm (2) having a first end (3) and a second end (4), a second arm (5) having a first end (6) and a second end (7), wherein the first arm (2) and the second arm (5) are joined together such that the distance between the first end (3) of the first arm (2) and the first end (6) of the second arm (5) is equal to the length of the cutting tool so that when, in use, the device (1) is aligned with an object to be cut the device indicates the cutting depth of the cutting tool. A method of indicating on an object to be cut the cutting depth of a cutting tool using such a device.

21 Claims, 11 Drawing Sheets

(56) References Cited

U.S. PATENT DOCUMENTS

| | | | | |
|---|---|---|---|---|
| 7,507,240 B2* | 3/2009 | Olsen | A61B 17/6416 | 606/57 |
| 7,682,362 B2* | 3/2010 | Dees, Jr. | A61B 5/103 | 33/512 |
| 7,695,476 B2* | 4/2010 | Nevelos | A61B 17/175 | 606/87 |
| 2002/0193801 A1* | 12/2002 | Marchione | A61B 17/175 | 606/96 |
| 2003/0028196 A1* | 2/2003 | Bonutti | A61B 17/025 | 606/87 |
| 2004/0092936 A1 | 5/2004 | Miller et al. | | |
| 2004/0230202 A1* | 11/2004 | Tromanhauser | A61B 17/1615 | 606/104 |
| 2005/0033290 A1* | 2/2005 | Nevelos | A61B 17/175 | 606/53 |
| 2005/0113841 A1* | 5/2005 | Sheldon | A61B 17/1668 | 606/88 |
| 2005/0209600 A1* | 9/2005 | Fencl | A61B 17/155 | 606/89 |
| 2005/0245934 A1* | 11/2005 | Tuke | A61B 17/15 | 606/79 |
| 2006/0058810 A1* | 3/2006 | Wozencroft | A61B 17/175 | 606/102 |
| 2006/0271058 A1* | 11/2006 | Ashton | A61B 17/175 | 606/96 |
| 2007/0173851 A1* | 7/2007 | McMillen | A61B 17/1764 | 606/87 |
| 2008/0287954 A1* | 11/2008 | Kunz | A61B 17/175 | 606/87 |

* cited by examiner

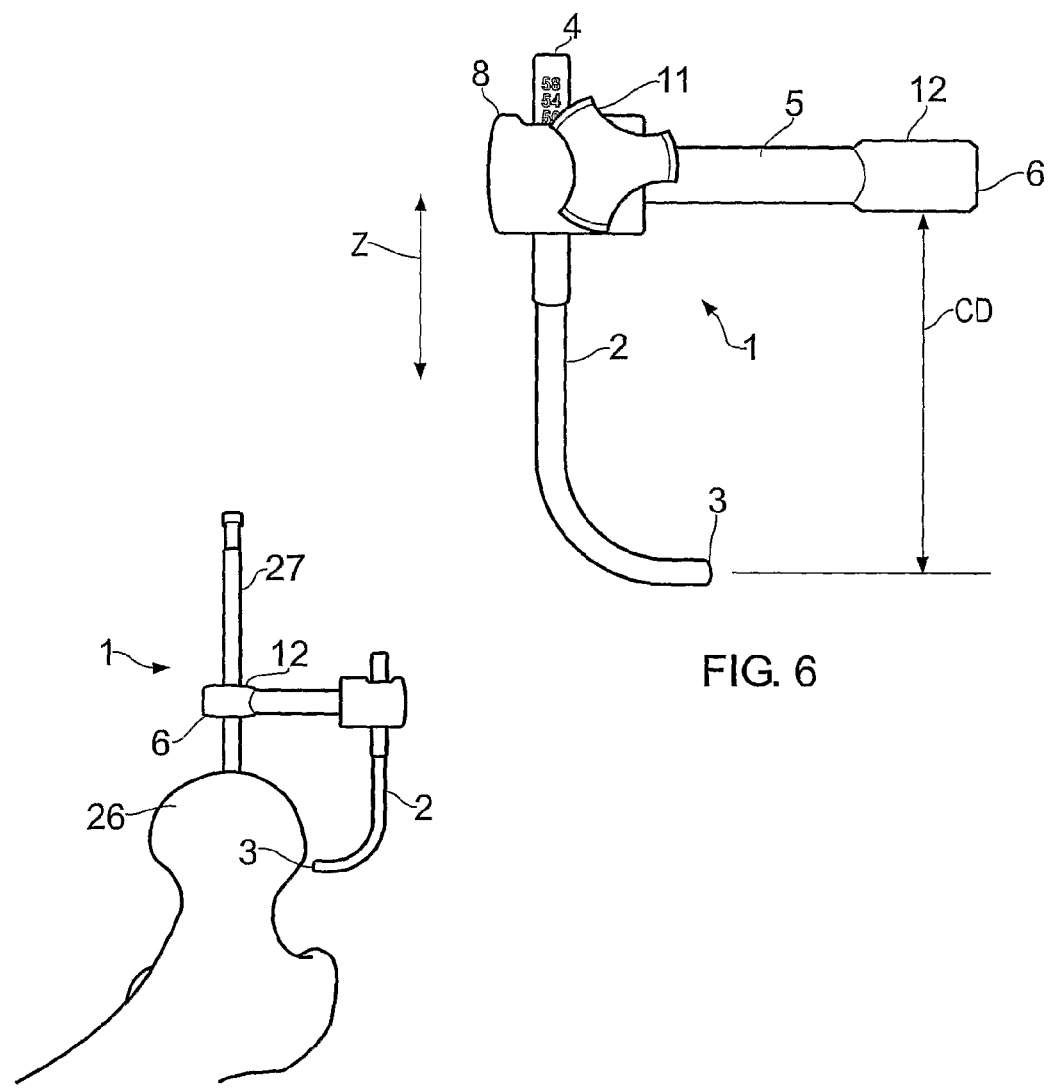
FIG. 6
FIG. 7
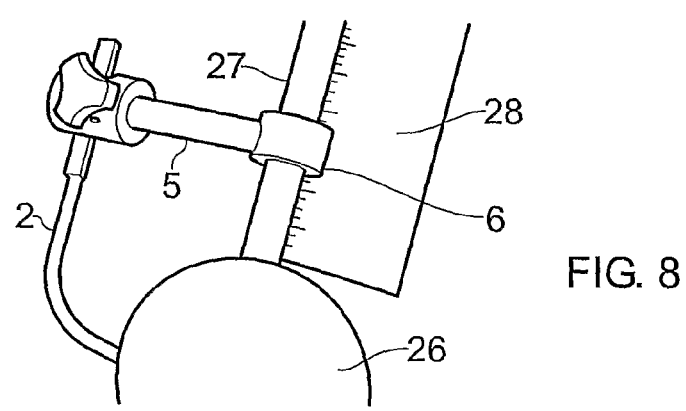
FIG. 8

MEDICAL DEVICE

CROSS REFERENCE TO RELATED APPLICATIONS

This application is the U.S. national phase of International Application No. PCT/GB2007/002763 filed on Jul. 19, 2007 and published in English on Jan. 24, 2008 as International Publication No. WO 2008/009959 A1 which application claims priority to Great Britain Application No. 0614428A filed on Jul. 20, 2006, the entire contents of both of which are incorporated herein by reference.

FIELD OF THE INVENTION

The present invention relates to a medical device, and more particularly a device for indicating on an object to be cut the cutting depth of a cutting tool.

BACKGROUND OF THE INVENTION

It is known to prepare the femoral head using a cutting tool such as a sleeve cutter. However, a problem encountered during preparation of the femoral head is that the sleeve cutter can over-shoot and notch the femoral neck. This may later result in a femoral neck fracture, requiring surgical revision.

SUMMARY OF THE INVENTION

It is therefore an aim of the present invention to prevent over-shooting of a cutting tool when used to cut an object.

There is provided a device for indicating on an object to be cut the cutting depth of a cutting tool. In a first embodiment, the device includes a first arm having a first end and a second end and a second arm having a first end and a second end. The first arm and the second arm are joined together such that the distance between the first end of the first arm and the first end of the second arm is equal to the length of the cutting tool so that when, in use, the device is aligned with an object to be cut the device indicates the cutting depth of the cutting tool.

The first and second arms of the device may be fixedly joined together.

The first and second arms of the device may be moveably joined together. For example, the second end of the first arm and the second end of the second arm may be hinged together. The hinge may be marked so that the angle between the first arm and the second arm can be set to a predetermined angle such that the distance between the first end of the first arm and the first end of the second arm is equal to the length of a particular cutting tool. The hinge may be marked with a specific reference numeral or other indicator that matches a reference numeral or other indicator on a corresponding cutting tool.

The device may further comprise a body which joins the first arm and the second arm.

There is also provided a second embodiment of a device for indicating on an object to be cut the cutting depth of a cutting tool. The device includes a body, a first arm moveably disposed in the body and having a first end and a second end, and a second arm disposed in the body and having a first end and a second end. In use, the first arm is disposed so that the distance between the first end of the first arm and the first end of the second arm is equal to the length of the cutting tool so that when the device is aligned with an object to be cut the device indicates the cutting depth of the cutting tool.

The device of embodiments of the present invention eliminates the risk of over-shooting and consequent notching. The device enables a method of physically controlling the travel of a cutting device to a predetermined depth to prevent over-shooting and possible notching. The device translates the cutting depth of the sleeve cutters on to the bone, thereby enabling the surgeon to visualize the position the sleeve cutter will reach during cutting in order to ensure that over-shooting is prevented.

The device is safe and easy to use. The device is suitable for use in both the posterior and anterior-lateral approaches.

In those embodiments in which the device is adjustable, the device may be adjustable to account for all sleeve cutter sizes.

Devices according to embodiments of the present invention may have any of the following features.

The distance between the first end of the first arm and the first end of the second arm may be measured parallel to the main axis of the first arm.

The first arm may be moveably disposed in the body such that, in use, the first arm is disposed so that the distance between the first end of the first arm and the first end of the second arm is equal to the length of the cutting tool so that when the device is aligned with an object to be cut the device indicates the cutting depth of the cutting tool.

The first arm and the second arm may be disposed substantially perpendicular to each other such that the first arm can move horizontally and/or vertically with respect to the second arm.

The second arm may be fixedly attached to the body, and the first arm may be moveably disposed in the second arm so that it can move horizontally and/or vertically within the second arm.

The second arm may be moveably disposed in the body.

The first arm may be partially curved so that the first end of the first arm is not co-linear with the remainder of the first arm.

The first end may be substantially perpendicular to the majority of the first arm.

The first end of the second arm may have an attachment means for attaching the device, in use, to an object.

The device may comprise a locking means for reversibly locking the first and/or second arms in a set position.

The device may comprise a mechanism such that at least one of the first arm and the second arm moves with respect to the body in a stepped motion. The mechanism may be a ratchet mechanism.

At least one of the first arm and the second arm may be resiliently biased with respect to the body. At least one of the first arm and the second arm may be spring-loaded with respect to the body.

The first arm may be marked so as to indicate the length of a corresponding cutting tool.

The second arm may be marked so as to indicate the width, radius or diameter of a corresponding cutting tool.

The first arm may be 50-100 mm long when measured parallel to the main axis of the arm between the first end and the second end. The first arm may be 60-90 mm long. The first arm may be 65-80 mm long. The first arm may be 65-75 mm long.

The first arm may have a width or diameter of 2-10 mm. The first arm may have a width or diameter of 2-8 mm. The first arm may have a diameter of 2-6 mm.

In those embodiments of the invention in which the first arm is partially curved, the lateral distance between the first end of the arm and the second end of the arm (measured from the main axis) may be 10-40 mm. The lateral distance may be 10-30 mm. The lateral distance may be 15-30 mm. The lateral distance may be 20-30 mm.

The second arm may be 30-100 mm long when measured parallel to the main axis of the arm between the first end and the second end. The second arm may be 30-80 mm long. The second arm may be 40-70 mm long. The second arm may be 40-60 mm long.

The second arm may have a width or diameter of 5-25 mm. The second arm may have a width or diameter of 5-20 mm. The second arm may have a width or diameter of 5-15 mm.

Devices according to the present invention may be made of plastic. The devices may be made of metal. The devices may be made of stainless steel.

There is also provided a methods of indicating on an object to be cut the cutting depth of a cutting tool. In one embodiment, the method includes selecting a cutting tool for cutting the object;
providing a device according to the first embodiment of the present invention, wherein the distance between the first end of the first arm and the first end of the second arm is equal to the length of the cutting tool; and
aligning the device with the object such that the device indicates the cutting depth of the cutting tool.

In an alternative embodiment, there is provided a method of indicating on an object to be cut the cutting depth of a cutting tool, the method comprising:

providing a device according to the second embodiment of the present invention;
selecting a cutting tool for cutting the object;
disposing the first arm of the device so that the distance between the first end of the first arm and the first end of the second arm is equal to the length of the cutting tool; and aligning the device with the object such that the device indicates the cutting depth of the cutting tool.

The object may be a bone. The bone may be a femur. The bone may have a guide rod and the first end of the second arm of the device may have an attachment means, such that the device is attached to the guide rod via the attachment means.

There is further provided a methods of cutting an object. In one embodiment, the method includes:

selecting a cutting tool for cutting the object, the cutting tool comprising a distal end having a cutting face and a proximal end;
providing a device according to the first embodiment of the present invention, wherein the distance between the first end of the first arm and the first end of the second arm is equal to the length of the cutting tool;
aligning the device with the object such that the device indicates the cutting depth of the cutting tool;
positioning the first end of the first arm at the maximum limit to which the cutting tool is to cut;
recording the position of the first end of the second arm relative to the object;
removing the device;
aligning the cutting tool with the object;
advancing the cutting tool so that the cutting face cuts the object;
stopping cutting when the proximal end of the cutting tool is aligned with the recorded position of the first end of the second arm.

In an alternative embodiment, the method includes providing a device according to the second aspect embodiment of the present invention;
selecting a cutting tool for cutting the object, the cutting tool comprising a distal end having a cutting face and a proximal end;
disposing the first arm of the device so that the distance between the first end of the first arm and the first end of the second arm is equal to the length of the cutting tool;
aligning the device with the object such that the device indicates the cutting depth of the cutting tool;
positioning the first end of the first arm at the maximum limit to which the cutting tool is to cut;
recording the position of the first end of the second arm relative to the object;
removing the device;
aligning the cutting tool with the object;
advancing the cutting tool so that the cutting face cuts the object;
stopping cutting when the proximal end of the cutting tool is aligned with the recorded position of the first end of the second arm.

Methods according to these embodiments of the present invention may have any of the following features.

The position of the first end of the second arm may be recorded by measuring the distance between the object and the first end, and the cutting tool may be advanced until the proximal end is separated from the object by the measured distance.

The position of the first end of the second arm may be recorded by placing a spacer on the end of the object, the spacer having a length that is equal to the distance between the object and the first end, and the cutting tool may be advanced until the proximal end contacts the spacer and is thereby prevented from advancing further.

The spacer may have fixed dimensions. The spacer may be hollow. The spacer may be solid.

The spacer may have a length (height) of 5-100 mm. The spacer may have a length of 10-80 mm. The spacer may have a length of 10-60 mm. The spacer may have a length of 10-40 mm. The spacer may have a length of 10-30 mm. The spacer may have a length of 10-20 mm.

The spacer may have a diameter of 10-40 mm. The spacer may have a diameter of 15-35 mm. The spacer may have a diameter of 20-30 mm.

The spacer may be adjustable in length so that the length of the spacer can be adjusted so that it is equal to the distance between the object and the first end of the second arm.

The spacer may be adjustable in length between 10-100 mm. The spacer may be adjustable in length between 10-80 mm. The spacer may be adjustable in length between 10-60 mm. The spacer may be adjustable in length between 10-40 mm. The spacer may be adjustable in length between 10-30 mm. The spacer may be adjustable in length between 10-20 mm.

The adjustable spacer may have a diameter of 10-40 mm. The spacer may have a diameter of 15-35 mm. The spacer may have a diameter of 20-30 mm.

The object may be a bone. The bone may be a femur. The bone may have a guide rod and the first end of the second arm of the device may have an attachment means, such that the device may be attached to the guide rod via the attachment means.

According to an embodiment of the present invention, there is provided a device in which the first and second arms are fixedly joined together such that the distance between the first end of the first arm and the first end of the second arm is fixed. The device may be used with corresponding cutting tools that all have the same length and therefore all have the same cutting depth. Accordingly, the device only has to translate a single cutting depth onto the object. A spacer may then be selected as appropriate in order to cut to the desired depth.

There is also provided a kit of parts that includes at least one device according to the first embodiment of the present invention and at least one spacer.

There is further provided a kit of parts that includes at least one device according to the second embodiment of the present invention and at least one spacer.

The kit of parts may comprise a plurality of spacers of different lengths.

The or each spacer may be adjustable in length.

The kit of parts may comprise at least one cutting tool.

BRIEF DESCRIPTION OF THE DRAWINGS

Reference will now be made, by way of example, to the accompanying drawings, in which:

FIG. 6 shows a side view of the device shown in FIG. 1;

FIG. 7 shows a side view of the device shown in FIG. 1 in use;

FIG. 8 shows a side view of the device shown in FIG. 1 in use;

DETAILED DESCRIPTION OF THE DRAWINGS

Figure 1:
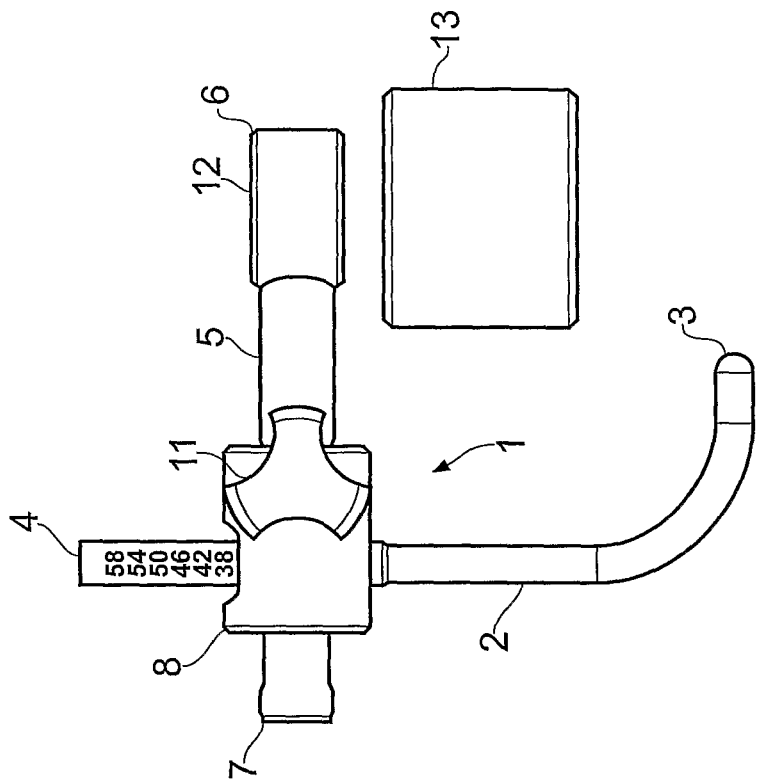
FIG. 1 shows a side view of a device according to an embodiment of the present invention.
Figure 2:
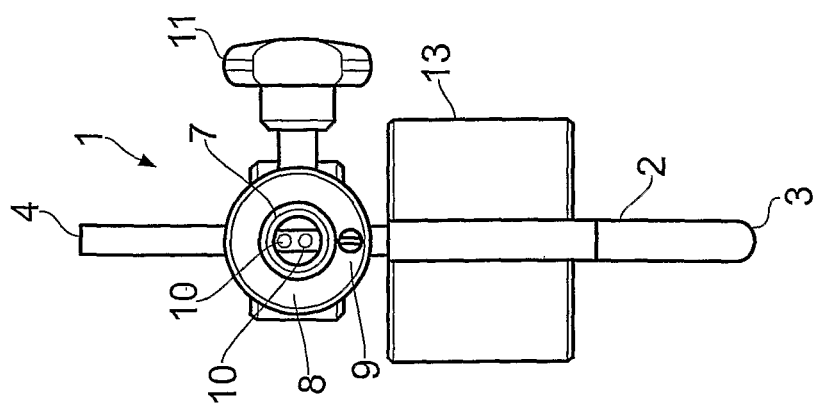
FIG. 2 shows an end view of the device shown in FIG. 1.

As shown in FIGS. 1 and 2, the device (1) comprises a first arm (2) having a first end (3) and a second end (4). The device has a second arm (5) having a first end (6) and a second end (7). The second arm (5) is attached to a body (8). The first arm (2) is moveably disposed in a slot (not shown) in the second arm (5) and in the body (8) such that the first arm (2) can move horizontally and vertically with respect to the second arm (5).

The body (8) can move horizontally along the second arm (5). The body (8) has a locking means in the form of a locking screw (11) which threads through the body (8) and bears on the second arm (5).

Figure 4:
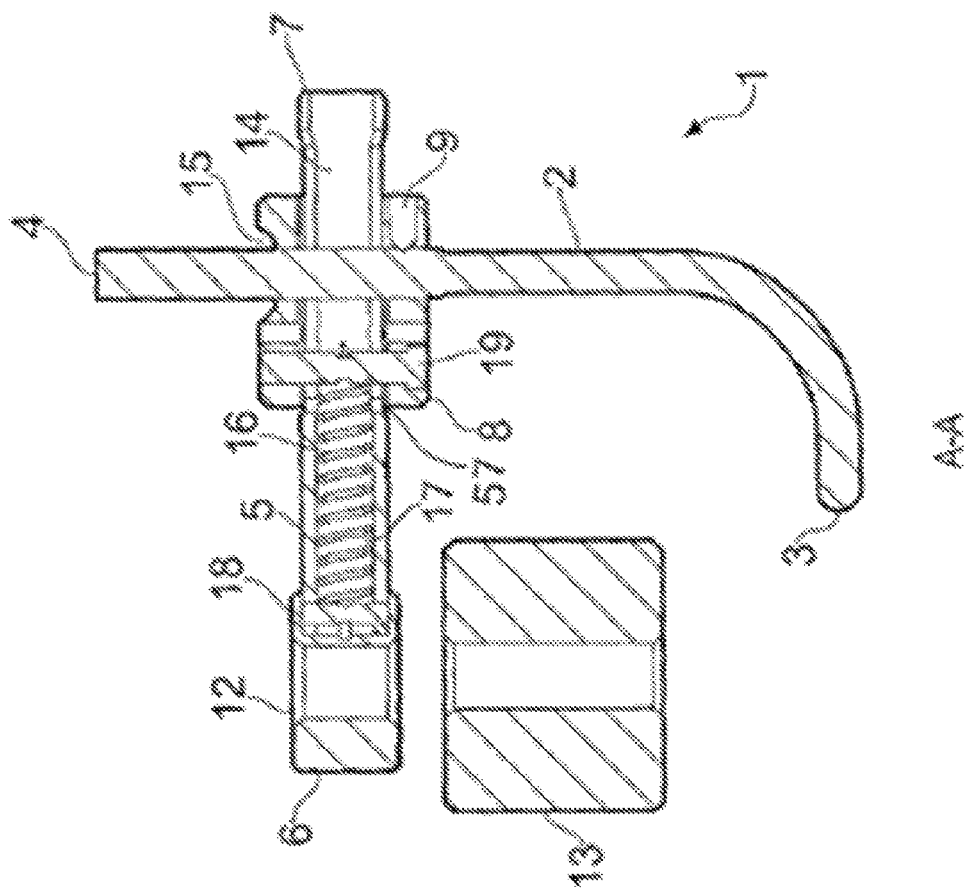
FIG. 4 shows a cross-section of the device shown in FIG. 3, taken along line A-A of FIG. 3.
Figure 3:
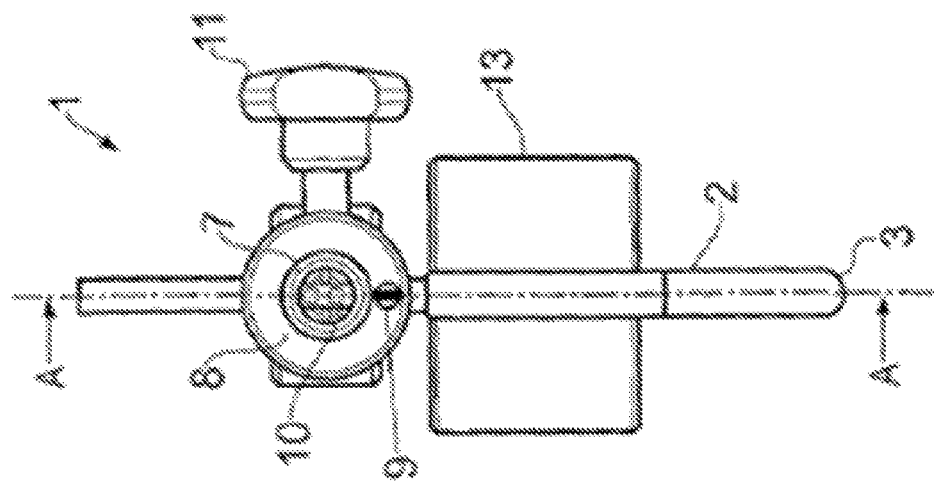
FIG. 3 shows an end view of a device according to an embodiment of the present invention.

As shown in FIGS. 2, 3 and 4, the body (8) has a plunger (9) which locates with a series of dimples (10) disposed at predetermined positions along the length of the first arm (2). The first arm can therefore be clicked into predetermined positions.

Figure 23:
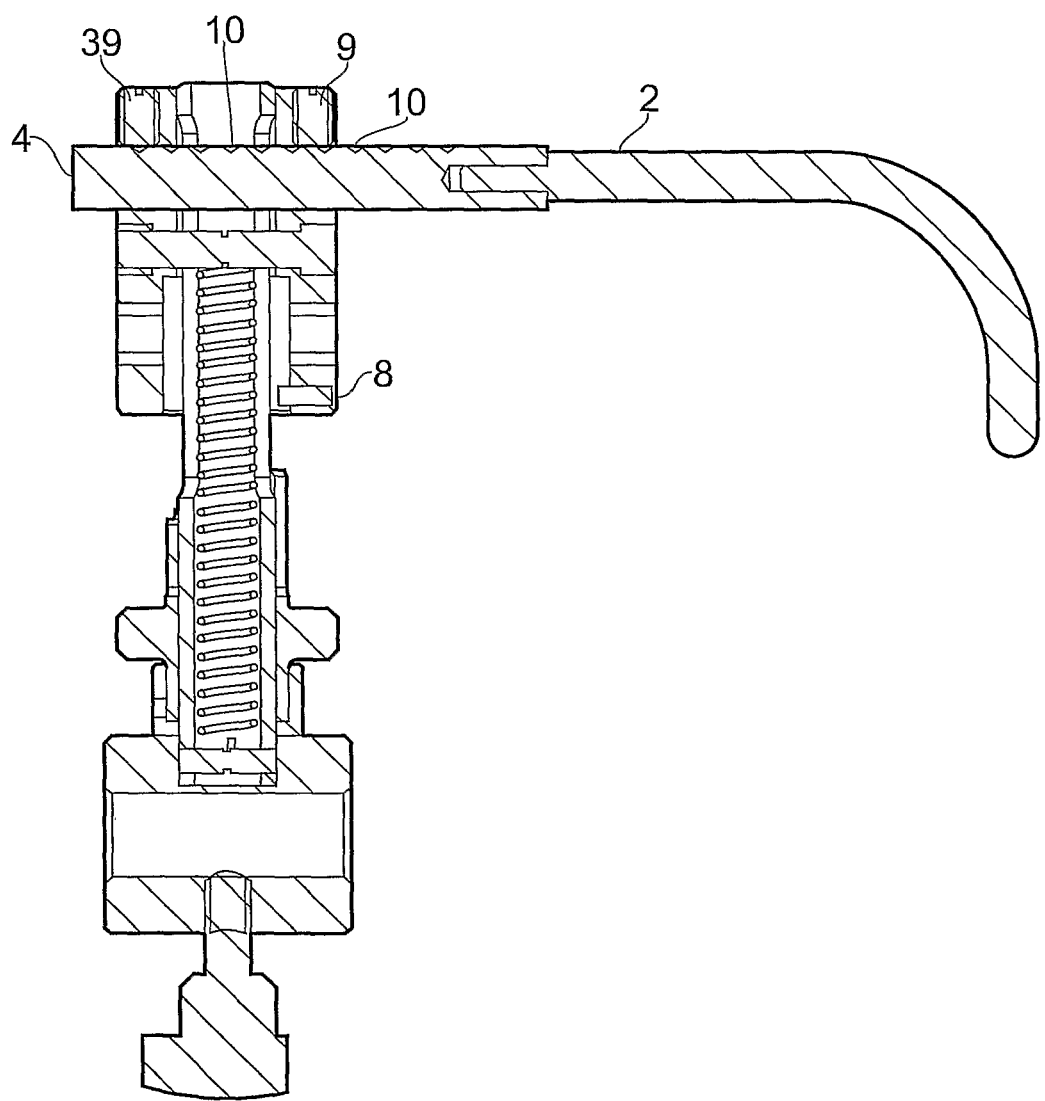
FIG. 23 shows a cross-section of a device according to an embodiment of the present invention.

As shown in FIG. 23, the body (8) may have two plungers (9, 39) which are offset with respect to each other such that only one of the plungers (9,39) locates in a dimple (10) at a time. This has the advantage that it enables the first arm to be clicked between predetermined positions in smaller steps.

The first end (3) of the first arm (2) is substantially perpendicular to the main part of the first arm (2). The first end (3) acts as a pointer in use, enabling the user to indicate on an object the cutting depth.

The second end (4) of the first arm (2) is marked so as to indicate the length of a corresponding cutting tool. When the device is used in connection with cutting a femoral head prior to implanting a femoral head implant, the markings on the first arm (2) may be settings that correspond to the appropriate sleeve cutter for the size of femoral head that is to be implanted. In the embodiment shown in FIG. 1, the numbers on the first arm (2) are indications of the spherical diameters of implant heads. They therefore relate to sleeve cutter dimensions (cutting depth and cutting radius) which are linked to the required preparation sizes of the bone to suit the internal geometry of the femoral head implant.

Figure 20:
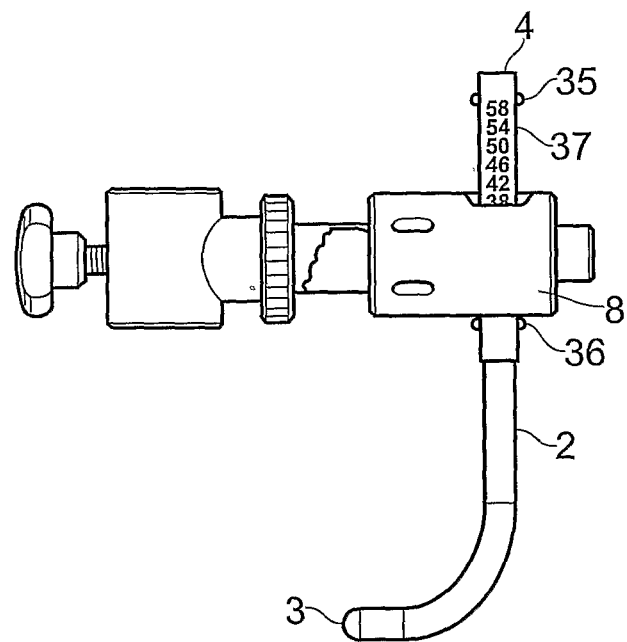
FIG. 20 shows a side view of a device according to an embodiment of the present invention.
Figure 21:
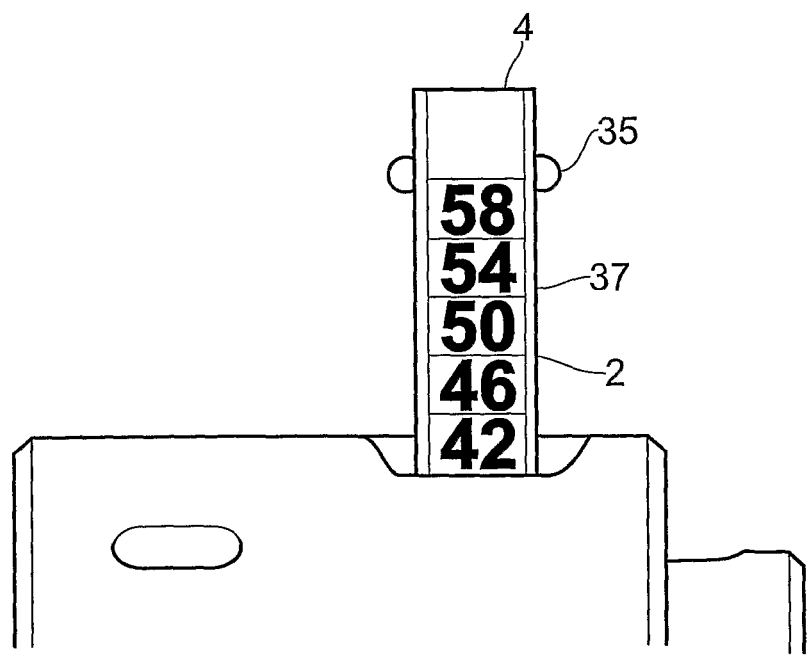
FIG. 21 shows an enlarged portion of the device shown in FIG. 20.
Figure 22:
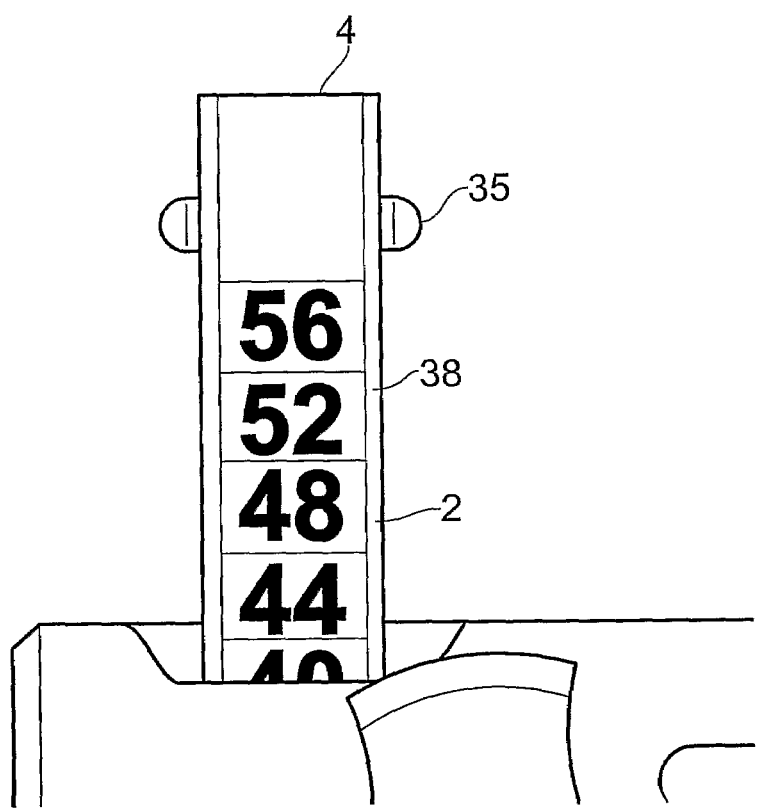
FIG. 22 shows an enlarged portion of the device shown in FIG. 20.

As shown in FIGS. 1, 20 and 21, in some embodiments of the present invention the second end (4) of the first arm (2) is marked at portion (37) with numbers 38, 42, 46, 50, 54, and 58 which correspond to the spherical diameters (in mm) of implant heads. As shown in FIG. 22, in some embodiments of the present invention the second end (4) of the first arm (2) is marked at portion (38) on the opposite side of the arm to portion (37) with numbers 40, 44, 48, 52, and 56 which also correspond to the spherical diameters (in mm) of implant heads. Thus, the device has 11 settings from 38 to 58 mm in 2 mm increments.

In alternative embodiments of the present invention, the range of diameters and the increments may be different. For example, the range of diameters may include diameters of less than 38 mm and more than 58 mm. The increment may be less than or more than 2 mm. For example, the increment may be 1 mm or 3 mm. The increment may be non-integer. For example, the increment may be 0.5 mm.

As shown in FIG. 20, in some embodiments of the present invention the first arm (2) has two cross pins (35,36). The pins (35,36) limit the travel of arm (2) in body (8), and prevent arm (2) from becoming detached from the device. The pins also indicate the upper and lower ranges of the spherical diameters of implant heads. In the embodiment shown in FIG. 20, when cross pin (35) contacts body (8), the device is set to correspond to an implant head spherical diameter of 58 mm. When cross pin (36) contacts body (8), the device is set to correspond to an implant head spherical diameter of 38 mm.

The first end (6) of the second arm (5) has an attachment means in the form of a hoop/ring (12) which can attach the second arm (5) to an object such as a bone or to a guide rod attached to a bone (see FIG. 7).

As shown in FIGS. 1 and 2, the device can be used with a spacer (13), as described in more detail with reference to FIGS. 9 to 11.

FIG. 4 shows a cross-section of a device (1) taken along line A-A of FIG. 3. As shown, the second arm (5) is moveably disposed in a first opening (57) of the body (8). The first arm (2) is moveably disposed in a slot (14) in the second arm (5) and a slot or second opening (15) in the body (8) such that the first arm (2) can move horizontally and vertically with respect to the second arm (5). The travel of the body (8) and first arm (2) along the second arm (5) is sprung-loaded by way of a fixed spring (16) which moves within a recessed hole (17) in the second arm (5). Cross pin (18) secures one end of the spring (16) to the second arm (5) and cross pin (19) secures the other end of the spring (16) to the body (8).

Figure 5:
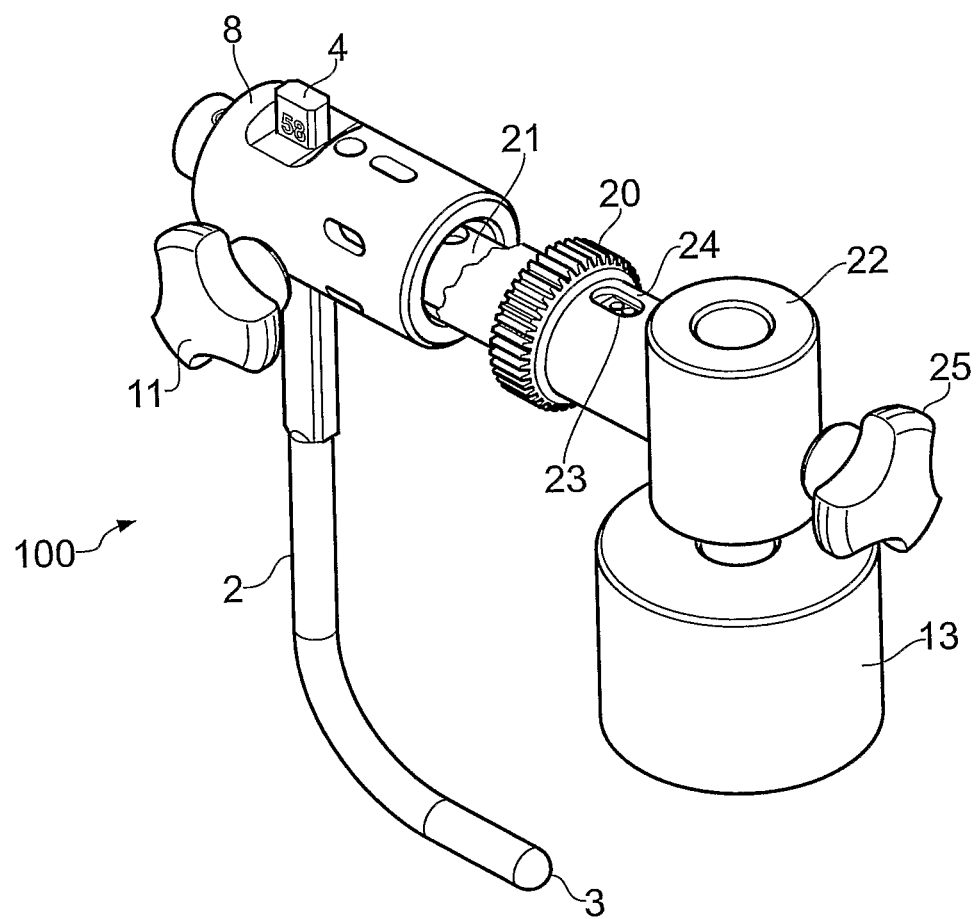
FIG. 5 shows an isometric view of a device according to an embodiment of the present invention.

FIG. 5 shows an isometric view of a device (100) according to another embodiment of the present invention. The device has a number of features in common with the device of FIGS. 1 to 4 and therefore the same reference numerals have been used for the common parts. The device shown in FIG. 5 has been modified to account for the diametric information of sleeve cutters. A stepper mechanism (20,21) has been added so that the position of the body (8) and therefore the first end (3) of the first arm (2) may be set relative to the central axis running through the attachment means (22). The distance between the first end (3) of the first arm (2) and the central axis can be set to equal the radius of a particular sleeve cutter. The recesses (21) in the stepper mechanism locate onto a pin (not shown) that passes through body (8) into the working space.

Settings (23) may be viewed through the aperture (24). The settings (23) are equivalent to the internal radius/diameter of each size of sleeve cutter. This information, along with the cutting depth, can then be transposed onto the bone prior to performing a cut.

The attachment means is in the form of an open cylinder (22) which can receive a guide rod. A locking screw (25) threads through the open cylinder (22) and bears on the guide rod. This enables the device (100) to be locked at various positions along the guide bar. This is useful when setting the device (100) to the correct height and determining spacer (13) size without loss of location.

FIGS. 6 to 11 show the device (1) of FIGS. 1 to 4 in use. As shown in FIG. 6, the first arm (2) of the device (1) can move vertically along the vertical axis (Z). The first arm (2) and the second arm (5) can move horizontally along the horizontal axis (X). The distance between the first end (3) of the first arm (2) and the first end (6) of the second arm (5) measured parallel to the main axis of the first arm (2) indicates the cutting depth (CD). Accordingly, a surgeon can set the cutting depth (CD) to match a selected sleeve cutter length by clicking the first arm (2) up and down in the body (8) until the desired sleeve cutter size is indicated on the scale on the second end (4) of the arm (2).

As shown in FIG. 7, the device (1) is firstly attached to the guide bar (27) by the attachment means (12) and passed over the bulk of the femoral head (26) by retracting the first arm (2) against the sprung-loaded mechanism (16). The first arm (2) may then be locked in the desired position using the locking screw (11).

The first arm (2) is then positioned vertically by aligning the first end (3) of the first arm (2) with the chosen cutting depth of the sleeve cutter. The first arm (2) is then rotated around the femoral head at this position to confirm the chosen cutting depth.

Once content with the chosen depth of cut the device (1) may be held in position and a ruler (28) used to measure the corresponding height from the zenith of the femoral head to the base of the first end (6) of the second arm (5), as shown in FIG. 8. A correspondingly sized spacer (13) is then selected. This step may also be performed without a ruler by placing selected spacers beneath the first end (6) of the second arm (5) until the desired position is achieved.

Figures 9, 10, 11:
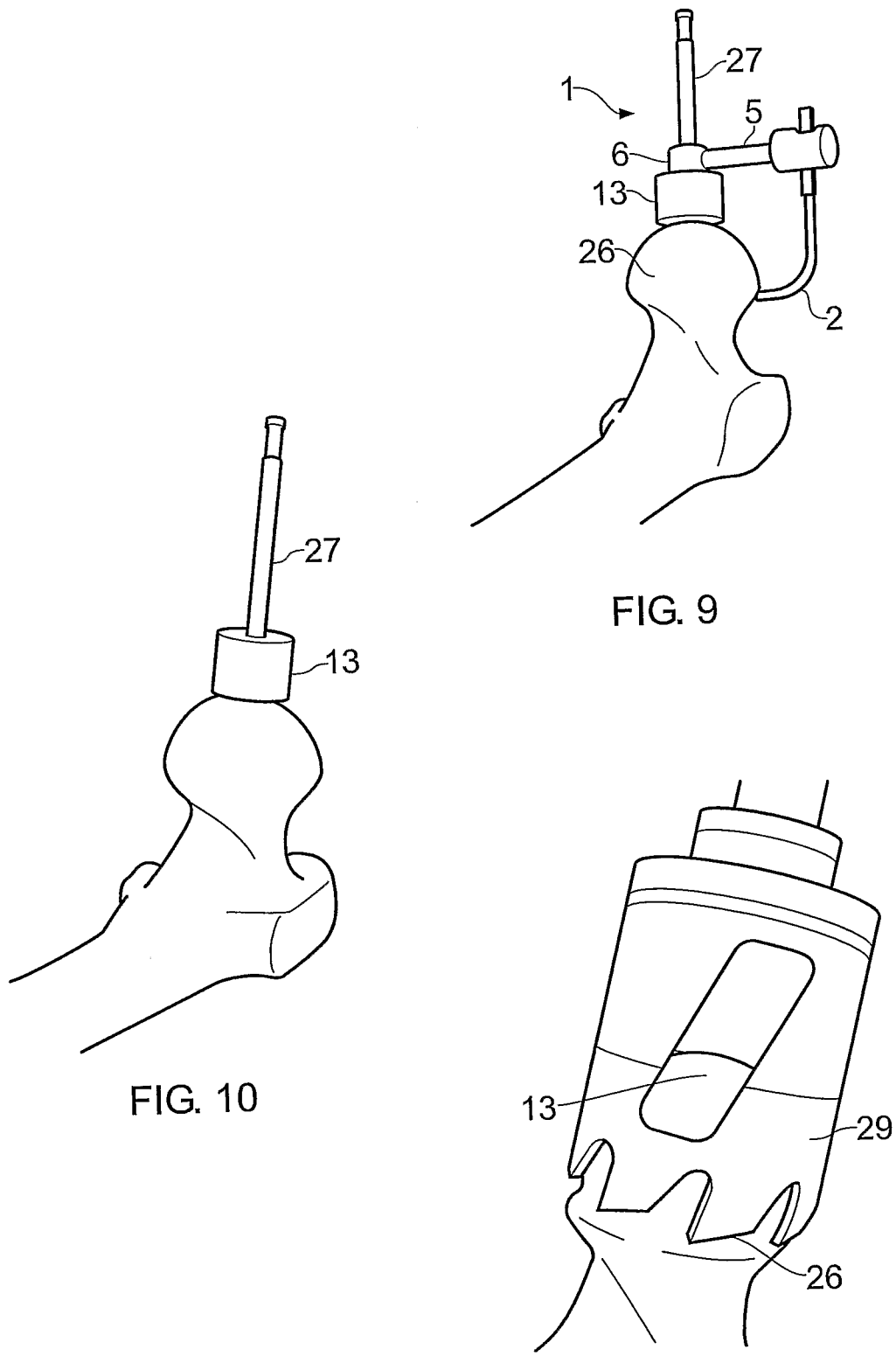
FIG. 9 shows a side view of the device shown in FIG. 1 in use.
FIG. 10 shows a side view of a femur having a guide rod inserted into it and a spacer disposed on the guide rod.
FIG. 11 shows a side view of a cutting tool in use.

Having measured the height and selected the particular spacer (13), the device (1) is removed from the guide bar (27) and reassembled onto the guide bar (27) with the selected spacer (13) beneath the first end (6) of the second arm (5), as shown in FIG. 9. The first arm (2) may again be rotated around the femoral head (26) to confirm the intended cut depth is correct.

The device (1) is then removed from the guide rod (27) and the spacer (13) is left in situ on the guide rod (27), as shown in FIG. 10.

As shown in FIG. 11, the selected sleeve cutter (29) is aligned with the guide rod (27) and it passes over the spacer (13) to perform the cutting operation. The spacer (13) acts as a physical stop when it contacts the proximal end of the sleeve cutter (29), thereby preventing the sleeve cutter (29) from travelling any further than the prescribed distance.

Figure 12:
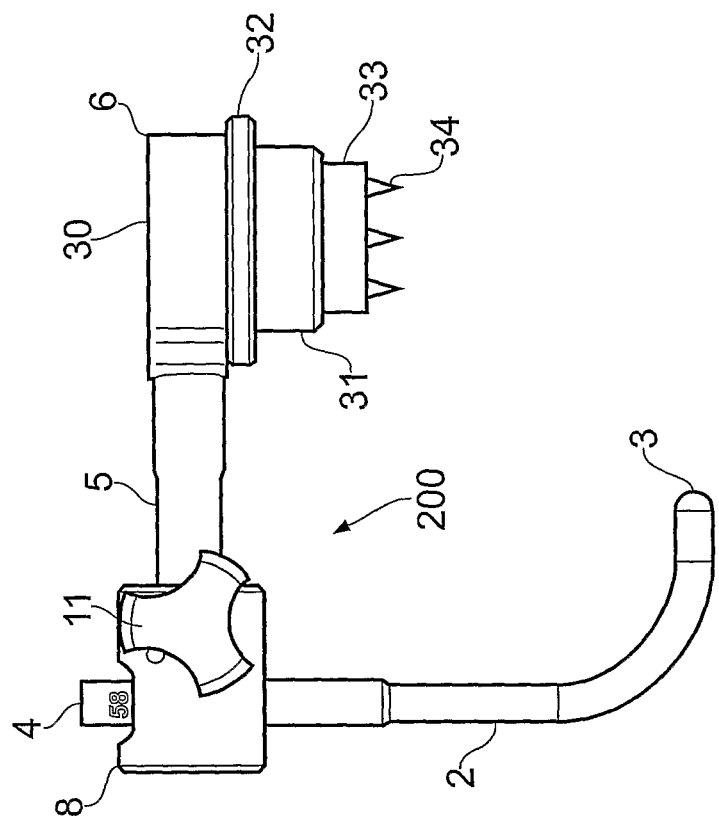
FIG. 12 shows a side view of a device according to an embodiment of the present invention.
Figure 13:
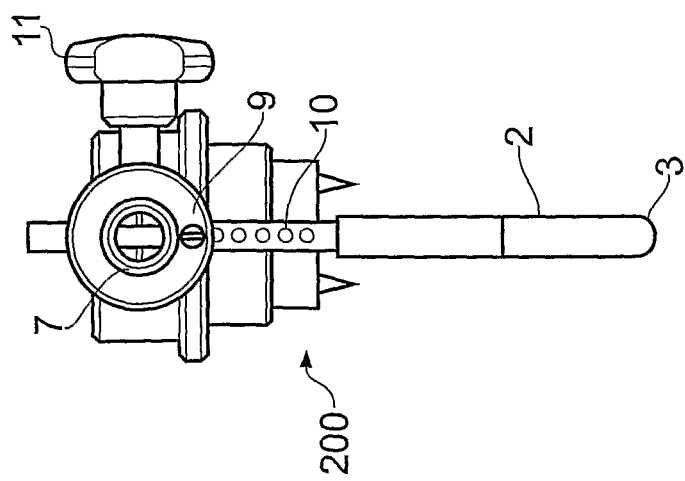
FIG. 13 shows an end view of the device shown in FIG. 12.

FIGS. 12 and 13 show a device (200) according to another embodiment of the present invention. The device has a number of features in common with the device (1) of FIGS. 1 to 4 and therefore the same reference numerals have been used for the common parts. The device (200) has been modified so that the first end (6) of the second arm (5) has an attachment means in the form of a hoop/ring (30) that receives an adjustable spacer (31). The adjustable spacer comprises two anti-clockwise threaded spacers, upper (32) and lower (33). The threaded spacers (32,33) screw in and out of each other, within a given height range. Three spikes (34) are provided on the base of the lower spacer (33). The spikes (34) can be used to fix the lower spacer (33) to an object such as a bone.

Figure 14:
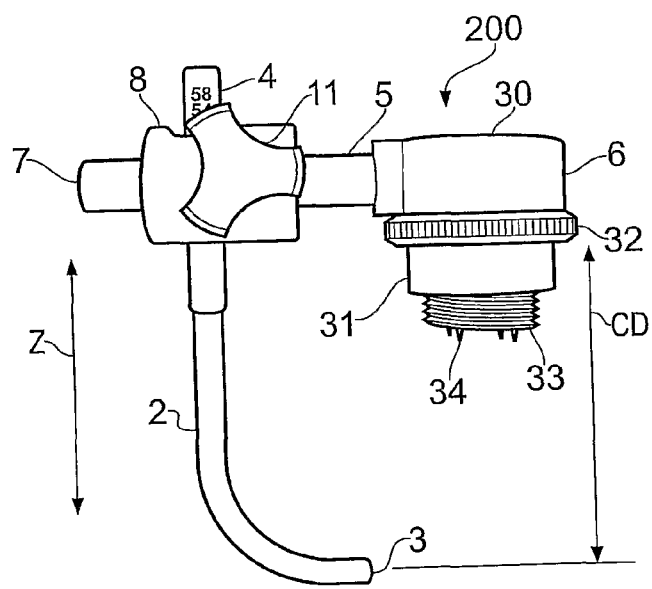
FIG. 14 shows a side view of the device shown in FIG. 12.

FIGS. 14 to 19 show the device (200) of FIGS. 12 and 13 in use. As shown in FIG. 14, the first arm (2) of the device (200) can move vertically along the vertical axis (Z). The first arm (2) and the second arm (5) can move horizontally along the horizontal axis as shown in FIG. 6. The distance between the first end (3) of the first arm (2) and the first end (6) of the second arm (5) measured parallel to the main axis of the first arm (2) indicates the cutting depth (CD). Accordingly, a surgeon can set the cutting depth (CD) to match a selected sleeve cutter length by clicking the first arm (2) up and down in the body (8) until the desired sleeve cutter size is indicated on the scale on the second end (4) of the arm (2).

Figure 15:
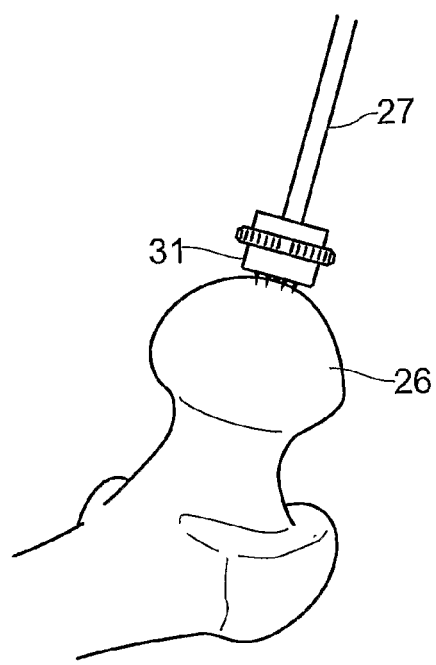
FIG. 15 shows a side view of a femur having a guide rod inserted into it and an adjustable spacer disposed on the guide rod.
Figure 16:
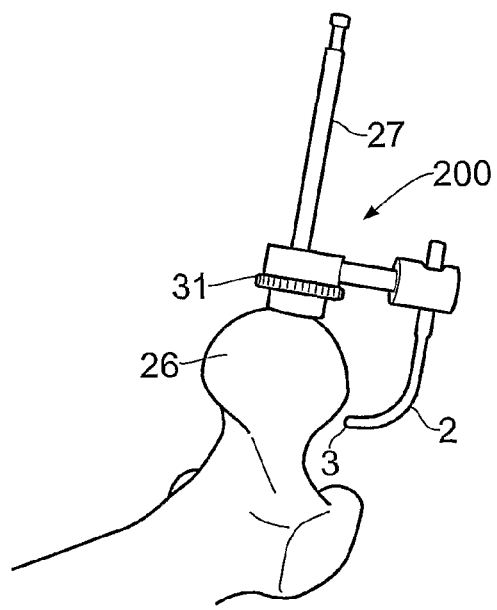
FIG. 16 shows a side view of the device shown in FIG. 12 in use.
Figure 17:
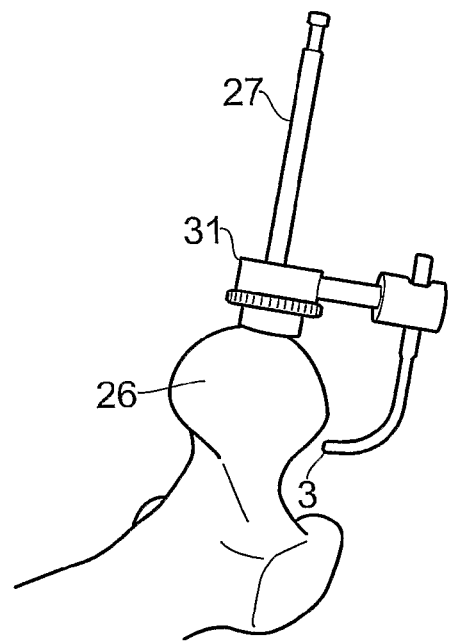
FIG. 17 shows a side view of the device shown in FIG. 12 in use.

As shown in FIG. 15, the adjustable spacer (31) is placed over the guide bar (27) and the spikes (34) are pressed firmly into the femoral bone. As shown in FIG. 16, the device (200) is then positioned on the adjustable spacer (31), with the first arm (2) passing over the bulk of the femoral head by retracting the first arm (2) using the sprung-loaded mechanism (16). The first arm (2) may then be locked in the desired position using the locking screw (11). As shown in FIG. 17, the device (200) is then positioned vertically by expanding the adjustable spacer (31) by rotating the upper spacer (32) clockwise until the first end (3) of the first arm (2) is aligned with the chosen cutting depth of the sleeve cutter (29). The first arm (2) is then rotated around the femoral head (26) at this position to confirm that the chosen depth of cut is correct.

Figure 18:
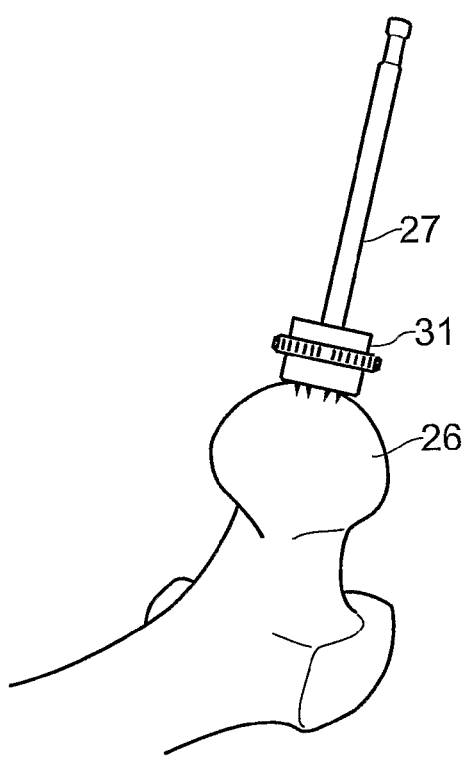
FIG. 18 shows a side view of a femur having a guide rod inserted into it and an adjustable spacer disposed on the guide rod.
Figure 19:
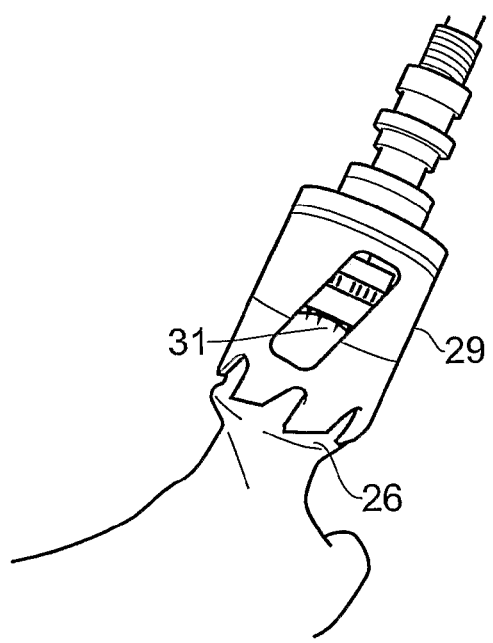
FIG. 19 shows a side view of a cutting tool in use.

As shown in FIG. 18, the device (200) is then removed and the adjustable spacer (31) left in situ. As shown in FIG. 19, the selected sleeve cutter (29) is aligned with the guide rod (27) and it passes over the spacer (31) to perform the cutting operation. The spacer (31) acts as a physical stop when it contacts the proximal end of the sleeve cutter (29), thereby preventing the sleeve cutter (29) from travelling any further than the prescribed distance.

The adjustable spacer (31) is threaded in an anti-clockwise direction so that it will not compress by the reaction of being pressed down upon by the clockwise rotating sleeve cutter (29) when it progresses to the end of its cut. The anti-clockwise thread will not turn against the downwards force applied.

The invention claimed is:

1. A device for indicating one or more sizes for cutting into an object by a cutting tool, the device comprising:

a first arm having an elongated main part, a first end, and a second end, the first and second ends of the first arm being positioned on opposite sides of the elongated main part, the second end of the first arm having markings to indicate a cutting size;

a second arm extending along a longitudinal axis between a first end and a second end of the second arm, the second arm having a second aperture sized to accommodate slideable displacement of the elongated main part within the second aperture as the first arm is displaced along a first axis and a second axis, the first axis being arranged perpendicular to the longitudinal axis, the second axis being arranged parallel to the longitudinal axis, the first end of the first arm extending away from the elongated main part in a direction that is parallel to the longitudinal axis; and a body having a first opening and a second opening, the first opening in communication with the second opening, the first opening sized to accommodate placement of the body about the second arm, the second opening sized to accommodate adjustable passage of the first arm through the body; and wherein the first end of the first arm and the first end of the second arm are separable by a distance substantially equal to a length of the cutting tool, and the first end of the first arm and a central axis of the second aperture in the second arm are separable by a plurality of discrete distances, each discrete distance being substantially equal to a cutting size such that when the device is aligned with the object to be cut, the device indicates the cutting size.

2. The device of claim 1, wherein the first end of the second arm is configured to couple the second arm to a guide bar.

3. The device of claim 2, wherein the body includes a locking device configured to selectively lock a position of the first arm relative to a position of the second arm.

4. The device of claim 3, further comprising a spring positioned to resiliently bias at least one of the first and second arms relative to the body.

5. The device of claim 4, wherein the spring is positioned within a recessed hole in the second arm, a first end of the spring is coupled to the body, and a second end of the spring is coupled to the second arm.

6. The device of claim 3, wherein the distance between the first end of the first arm and the first end of the second arm is measured parallel to a main axis of the elongated main part.

7. The device of claim 6, wherein the second arm is fixedly attached to the body.

8. The device of claim 6, wherein the first opening of the body is sized to accommodate linear displacement of the body relative to the second arm in a direction parallel to the longitudinal axis.

9. The device of claim 1, wherein the cutting size indicated by the markings is at least one of a width, a radius, a length, and a diameter of the cutting tool.

10. A device for indicating one or more sizes for cutting into an object by a cutting tool, the device comprising:

a first arm extending between a first end and a second end, the first end is not co-linear with the second end;

a second arm extending between a first end and a second end along a longitudinal axis, the second arm having a second aperture sized to accommodate displacement of the first arm along a first axis and a second axis, the first axis being arranged perpendicular to the second axis; and a body having a first opening and a second opening, the first opening sized to accommodate placement of the body about the second arm, the second opening in communication with the second aperture and sized to accommodate adjustable displacement of the first arm about the second aperture along the first and second axes, the body further including a locking device structured to lock a position of the first arm about the first and second axes relative to the second arm; and wherein the first end of the first arm and the first end of the second arm are selectively separable by a distance substantially equal to a length of the cutting tool, and wherein the first end of the first arm and a central axis of the second aperture are separable by a plurality of discrete distances, each discrete distance being substantially equal to a cutting size of the cutting tool such that when the device is aligned with an object to be cut, the device indicates one or more sizes of the cutting tool.

11. The device of claim 10, wherein the first arm includes a first cross pin and a second cross pin, the first and second cross pins positioned on opposite sides of the second aperture and sized to prevent removal of the first arm from the second aperture.

12. The device of claim 10, wherein the first and second arms are moveably joined to one another.

13. The device of claim 10, wherein the first opening of the body is sized to accommodate linear displacement of the body relative to the second arm.

14. The device of claim 13, wherein the second end of the first arm includes a plurality of markings indicative of a size of the cutting tool, the size comprising at least one of a width, a radius, a length, and a diameter of the cutting tool.

15. The device of claim 10, wherein the body includes a ratchet mechanism configured for incremental stepped displacement of at least one of the first and second arms relative to the body.

16. A kit of parts comprising at least one device of claim 10, the kit further comprising at least one spacer, and wherein at least one of the at least one spacers has a length that extends between a base of the first end of the second arm and the object.

17. The kit of parts of claim 16, the kit further comprising a cutting tool having a proximal end, wherein the proximal end is positioned to engage the at least one spacer when the cutting tool cuts to a predetermined depth in the object.

18. The kit of parts of claim 16, wherein the at least one spacer comprises a spacer having an adjustable length.

19. The device of claim 10, wherein the body includes a first plunger sized to be selectively located in one or more of a plurality of dimples disposed at predetermined positions along a length of the first arm.

20. The device of claim 19, wherein each of the predetermined positions corresponds to a cutting depth of the cutting tool.

21. The device of claim 20, wherein the body includes a second plunger sized to be selectively located in one or more of the plurality of dimples, the second plunger being offset from the first plunger such that the first and second plungers cannot both be concurrently located in one or more of the plurality of dimples.

* * * * *